United States Patent [19]

Chittenden

[11] 4,342,313

[45] Aug. 3, 1982

[54] CATHETER INSERTION DEVICE

[75] Inventor: Richard M. Chittenden, Grayslake, Ill.

[73] Assignee: Abbott Laboratories, NorthChicago, Ill.

[21] Appl. No.: 237,319

[22] Filed: Feb. 23, 1981

[51] Int. Cl.³ .............................................. A61M 5/00
[52] U.S. Cl. ................................... 128/214.4; 128/348
[58] Field of Search .............. 128/214.4, 214, 349–350

[56] References Cited

U.S. PATENT DOCUMENTS

| | | | |
|---|---|---|---|
| 3,561,445 | 2/1971 | Katerndahl et al. | 128/214.4 |
| 3,995,628 | 12/1976 | Gula et al. | 128/214.4 |
| 4,106,506 | 8/1978 | Koehn et al. | 128/214.4 |
| 4,160,451 | 7/1979 | Chittenden | 128/214.4 |

Primary Examiner—Stephen C. Pellegrino

Attorney, Agent, or Firm—Robert L. Niblack; Robert S. Beiser

[57] ABSTRACT

The invention relates generally to an improved catheter insertion device of the type having a drum-like receptacle which advances the catheter when it is rotated relative to the base, causing the catheter to move through a tubular outlet. The improvement comprises a removable needle which extends coaxially through a tubular housing tangentially affixed to the dispenser. A flexible cannula telescopically surrounds the distal portion of the needle. The cannula is connected to a catheter outlet from the receptacle and is adapted to be inserted into the vein of a patient during venipuncture. Once venipuncture is performed, the needle is slidably removed from the cannula and catheter outlet, and the catheter is telescopically inserted into and through the cannula and thereby into the vein of the patient. The base and receptacle may then be easily separated and removed from the catheter.

15 Claims, 6 Drawing Figures

U.S. Patent  Aug. 3, 1982  Sheet 1 of 2  4,342,313
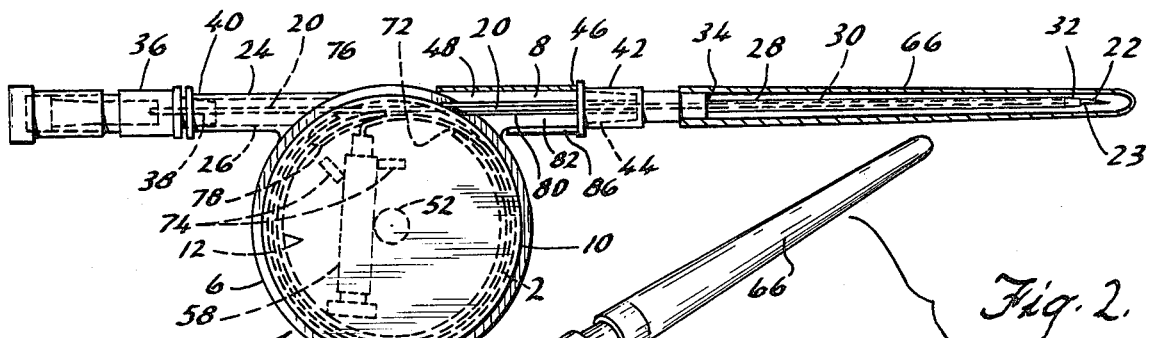
Fig. 1.
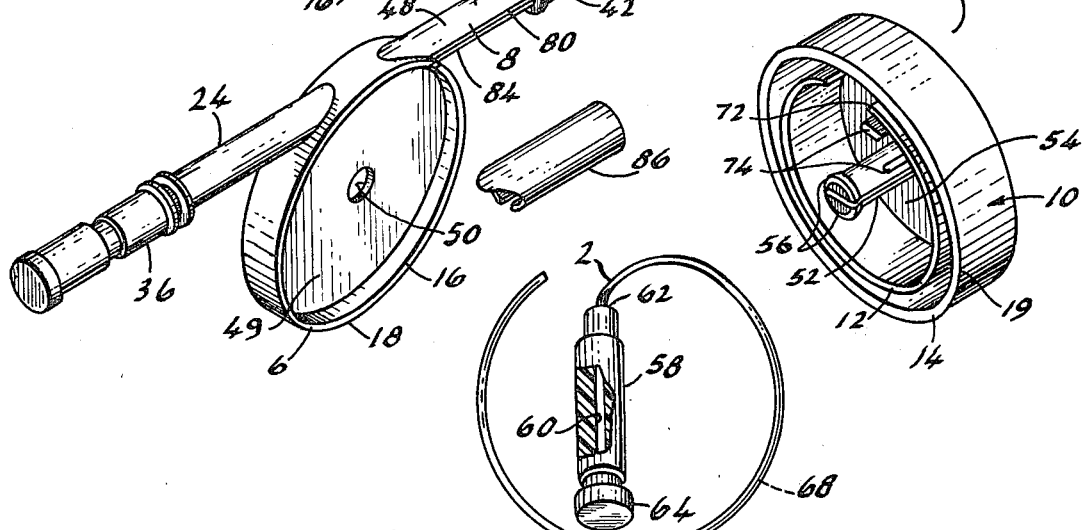
Fig. 2.
Fig. 3.
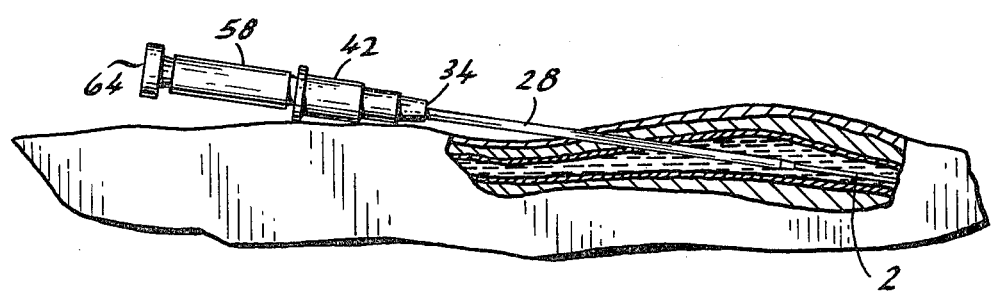
Fig. 4.

CATHETER INSERTION DEVICE

BACKGROUND OF THE INVENTION

This invention relates generally to devices used to implant catheters in a recipient, and more particularly to the implanting of relatively long catheters. The invention also relates to units adapted to store catheters for use in venipuncture, and after venipuncture to advance a long catheter into the patient while maintaining the aseptic condition of the catheter.

Generally, catheters now in use for intravenous applications may be classified as "needle-inside" or "needle-outside". These classifications result from the provision of a needle concentrically arranged with respect to a catheter to be placed in the vein of a patient. This concentric arrangement has been found to be relatively satisfactory, but does result in certain problems. For example, ordinarily it is necessary to provide access to the body through an incising element, then to provide a conduit for fluid passage using a hollow tube or catheter. Using a single element as the incising element and conduit is not recommended due to the danger of internal damage when the needle or incising element is left in place. Accordingly, the concentric arrangement of incising element and conduit is utilized. However, a long catheter arranged outside the needle is likely to be contaminated and is difficult to advance into the vein.

A particular problem has been found in devices of this kind in effectively removing the needle both from the venipuncture device and from the site following venipuncture. While the needle remains in the patient, there is a possibility of injury to the vein of the patient. Similarly, once the catheter has been inserted and the needle slidably removed from the patient, there remains the danger of the needle puncturing the catheter. Likewise, during insertion, when the catheter hits a restriction, many times the catheter is pulled back, increasing the risk of being cut by the needle heel.

A number of catherter insertion devices now available provide for the storage of long, flexible catheters within a drum-like receptacle. When the receptacle is rotated relative to its base, the catheter is advanced through the external needle. This method is used after venipuncture to advance the catheter into the patient. A problem remains, however, in removing the needle and catheter insertion device after venipuncture. In one present device, disclosed in U.S. Pat. No. 3,561,445, the needle is slid rearwardly on the catheter to the area proximate the catheter hub. The needle cannot be entirely removed, however. In another device, disclosed in U.S. Pat. No. 3,995,628, a slit needle is used and the catheter withdrawn from the needle. However, in both cases there is a danger of cutting or perforating the catheter, and the removal process is difficult and messy.

Accordingly, it is an advantage of the present invention to provide an improved needle-inside catheter insertion device in which the needle may be removed from the patient immediately following venipuncture, while retaining access to the vein of the patient for insertion of a long catheter.

It is an additional advantage of the present invention to provide such a device in which the catheter may be readily and easily advanced into the patient without manually engaging the catheter.

Still another advantage is to provide a catheter dispenser which may be discarded after the catheter is implanted, in order to facilitate the connection of extrinsic equipment and to ensure the patency of the catheter.

These and other advantages of the invention will become apparent from a consideration of the specification and claims.

SUMMARY OF THE INVENTION

The foregoing advantages are accomplished, and the shortcomings of the prior art are overcome by the catheter insertion device of the present invention, which comprises a catheter dispenser having a base with an outlet extending therefrom and a drum-like catheter receptacle, engaged to the base in rotating relationship. When the catheter receptacle is rotated relative to the base the catheter is caused to be threadably moved through the outlet. The base and receptacle are separable so that the dispenser may be removed from the catheter following dispensing of the catheter into the vein of the patient.

The improvement of the present invention over the prior art comprises an elongated piercing member or needle coaxially disposed through a tubular housing which extends tangentially from the catheter dispenser, and through a tubular and catheter outlet oppositely disposed from the tubular housing. A cannula or flexible tube continuously and telescopically surrounds the distal portion of the needle from the end of the catheter outlet to the area proximate the sharpened tip. The proximal end of the cannula is connected with the catheter outlet. Preferably, the cannula is beveled at its distal end so as to allow simultaneous introduction of the needle and cannula into the vein of the patient without undue discomfort or injury. Following venipuncture, unlike the prior art, the needle may be slidably removed from the cannula, catheter outlet, and tubular housing. The catheter may then be telescopically inserted into and through the catheter outlet and cannula and hence into the vein of the patient.

The previously mentioned tubular housing may also include a female hub member extending therefrom and in fluid tight connection therewith. The female hub telescopically receives the previously mentioned male hub, which is pressfit therein so as to selectively hold the needle in place within the tubular housing, but also allow relatively easy removal of the needle. Similarly, the cannula may be constructed with a coupling socket having an axial bore therethrough, fixedly attached to its proximal end. The coupling socket is designed for telescopic reception of and press-fit connection to the distal end of the catheter outlet. As a result, the cannula may be removed from the device after venipuncture. The catheter preferably has a hub attached at its proximal end adapted for connection to a variety of I.V. devices.

In one embodiment, the catheter outlet comprises a cylindrical passage integrally molded in the base and in coplanar relationship thereto. The cylindrical passage is parallel in curvature at its first end to the periphery of the base and extends tangentially therefrom. The cylindrical passage serves as a lumen for guiding the catheter out of the dispenser.

In order to remove the catheter from the device, the catheter outlet also includes a slot axially disposed along one side and adapted for selective removal of the catheter. This slot facilitates complete separation of the catheter from the dispenser following introduction of the catheter into the vein of the patient. The catheter outlet may be constructed of a resilient material, or the top and bottom portions of the outlet may be connected by hinges or snap-fit lugs to allow such removal. As a result, the upper and lower portions are resiliently openable and resealable as required. In those cases where the slot is open, a cover may be selectively attached to seal the slot.

A tubular needle sheath is coaxially disposed about the cannula and distal portion of the needle. The needle sheath is telescopically insertable onto the distal end of the catheter outlet so as to enclose and protect the cannula and needle until the period of use.

BRIEF DESCRIPTION OF THE DRAWINGS

FIG. 1 of the drawings is a side view of the assembled catheter insertion device according to the present invention.

FIG. 2 of the drawings is an exploded perspective view of the catheter dispenser of FIG. 1.

FIG. 3 of the drawings is a side view partially broken away of the catheter of FIG. 1 with appurtenant catheter hub.

FIG. 4 of the drawings is a side view, partly in section, of the catheter implanted in a patient wherein the catheter hub extends from the catheter and the catheter dispenser has been discarded.

DETAILED DESCRIPTION OF THE PREFERRED EMBODIMENT

Figure 5:
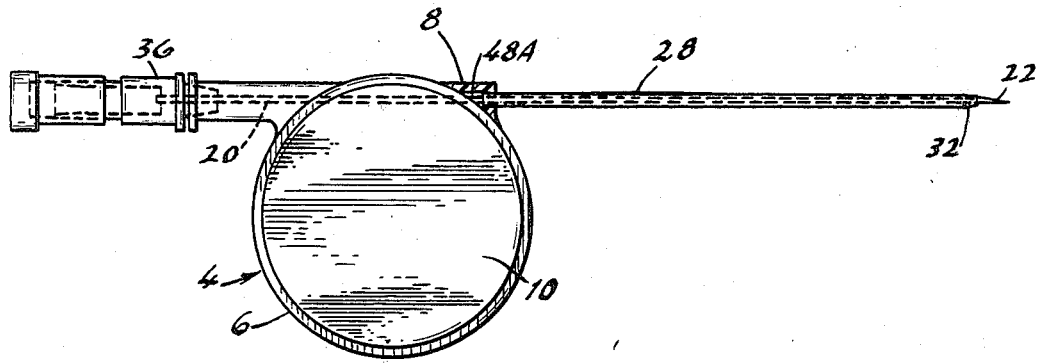
FIG. 5 of the drawings is a vertical section of an alternative embodiment of the catheter insertion device of FIG. 1.

While this invention is susceptible of embodiment in many different forms, there is shown in the drawings and will herein be described in detail, several specific embodiments with the understanding that the present disclosure is to be considered as an exemplification of the principles of the invention and is not intended to limit the invention to the embodiments illustrated.

The improved catheter insertion device illustrated in the present invention, as best seen in FIGS. 1 and 2 comprises, in its simplest form, a catheter 2 coiled within a catheter dispenser 4 having a base 6 with a catheter outlet 8 extending therefrom and a catheter receptacle 10 adapted for receiving catheter 2. Catheter receptacle 10 has an inwardly facing wall 12 for receiving catheter 2 therein and mechanically engaging same. The dispenser may include a snap-fit means 56 for engaging the base and receptacle in rotating relation. As shown in FIG. 2, snap fit means 16 may comprise a peripheral rim 18 having an inner diameter approximately the same as an outer bead 19 of peripheral wall 14 of receptacle 10. This size relationship allows receptacle 10 to snap onto and rotatably fit within base 6 in its assembled state. Catheter 2 is mechanically engaged with receptacle 10 so that rotation of receptacle 10 relative to base 6 causes catheter 2 to be threadably moved through outlet 8. Other commonly known means of rotatably connecting base 6 and receptacle 10 are disclosed infra.

The present application is an improvement over the prior art in the inclusion of an elongated piercing means or needle 20 having a sharpened tip 22 at its distal end 23 coaxially disposed through tubular housing 24 and through catheter outlet 8. Tubular housing 24 has an axial bore 26 extending longitudinally therethrough, is tangentially affixed to catheter dispenser 4 and is coaxially aligned to and oppositely disposed from catheter outlet 8.

In addition to the inclusion of needle 20, catheter dispenser 4 is distinguished from the previously mentioned Katerndahl reference, U.S. Pat. No. 3,561,445 by the inclusion of a cannula member 28 continuously and telescopically surrounding the distal portion 30 of needle 20 which extends beyond catheter outlet 8. Cannula 28 extends to the area proximate sharpened tip 22, but does not extend over the tip in order to allow venipuncture. The distal end 32 of cannula 28 is beveled proximate sharpened tip 22 so that needle 20 and cannula 28 puncture the skin of the patient substantially simultaneously. Following venipuncture, needle 20 is slidably removed from cannula 28 and from catheter outlet 8. Catheter 2 is then telescopically inserted into and through catheter outlet 8 and cannula 28 and hence into the vein of the patient. Since cannula 28 is constructed of a flexible, resilient material, once needle 20 is removed, the danger of injury to the patient or skiving of the catheter is similarly obviated. The proximal end 34 of cannula 28 is connected to catheter outlet 8 and is coaxially aligned thereto.

In a preferred embodiment, a male hub member 36 is affixed to the proximal end 38 of needle 30 and has an exterior shape adapted for mating engagement with the distal end 40 of tubular housing 24. By this it is meant, that the outside diameter of the male hub 36 is substantially the same size as axial bore 26, or tapered so that male hub 36 may be press-fit into axial bore 26. Conversely, male hub 36 may easily be grasped and removed from axial bore 26, thereby slidably removing needle 20 from catheter dispenser 4.

As an additional feature, cannula 28 may include a cannula coupling socket 42 with an axial bore 44 extending longitudinally therethrough. Coupling socket 42 is fixedly attached in fluid-tight connection to cannula 28 at the proximal end 34 thereof and is adapted by means of axial bore 44 for telescopic reception of and press-fit connection to the distal end 46 of catheter outlet 8. As a result, cannula 28 may be selectively removed from the device, as required.

As further seen in FIGS. 1 and 2, catheter outlet 8 preferably comprises a tubular member 48 tangentially connected and opening into base 6. When the dispenser is assembled, tubular member 48 is in coaxial alignment with and oppositely disposed from, tubular housing 24. Needle 20 extends coaxially through tubular housing 24 and tubular member 48. However, in an alternative embodiment, best seen in FIG. 5 of the drawings, catheter outlet 8 may comprise an opening 48A from base 6 which permits the passage of catheter 2. In this embodiment, cannula 28 is attached directly to receptacle 10, but is removable therefrom.

As best seen in FIG. 2 of the drawings, base 6 preferably includes a wall 49 having a central aperture 50 concentrically disposed therein. A spindle 52 is coaxially disposed within receptacle 10 and is adapted to extend through aperture 50. As shown, spindle 52 is disposed on outer wall 54 which substantially closes one end of receptacle 10. Spindle 52 further includes a plurality of projections 56 which extend through aperture 50 when base 6 is positioned on receptacle 10, so as to retain base 6 thereon, but allow rotation of receptacle 10.

Along these same lines, as best seen in FIG. 3, a catheter hub 58 having an axial bore 60 extending longitudinally therethrough is affixed and in fluid connection to catheter 2 at its proximal end 62. Catheter hub 58 has a plug 64 affixed at its proximal end and extending into axial bore 60. Upon removal of plug 64 a variety of intravenous devices such as male Luer fitments may be inserted into axial bore 60 so as to connect catheter 2 to various I.V. solutions, electronic monitoring devices, or other commonly known I.V. devices. In order to allow access to hub 58, as best seen in FIG. 2 of the drawings, in a preferred embodiment, receptacle 10 is selectively separable from base 6 so that catheter 2 may be removed from dispenser 4 subsequent to dispensing of catheter 2 into the vein of the patient. This allows easier access to catheter hub 58. Dispenser 4 may include a tubular needle sheath 66 coaxially disposed about cannula 28 and the distal portion 30 of needle 20. Needle sheath 66 is telescopically insertable onto the cannula coupling socket 42 so as to enclose and protect cannula 28 and distal portion 30 of needle 20.

As noted previously, catheter 2 is spirally wound within inwardly facing wall 12 of receptacle 10 and extends through dispenser outlet 8. In one embodiment, a stiffener or stylet 68 extends through the catheter urging the catheter against inwardly facing wall 12 so as to facilitate dispensing of catheter 2. The tendency of catheter 2 to uncoil forces it against peripheral wall 12 so that movement of wall 12 by manually rotating receptacle 10 results in the catheter moving also. In all cases, when the catheter is threaded through opening 72 in inner wall 12, revolving of receptacle 12 with respect to base 6 will force the coiled catheter out of receptacle 4 and into the catheter outlet 8 and cannula 34.

As further seen in FIGS. 1 and 2, dispenser 4 may include a plurality of lugs 74 disposed at right angles from receptacle 10 in dispenser 4. Lugs 74 are constructed of the proper shape and located so as fixedly position hub 58 within receptacle 10 against spindle 46. As a result, rotation or receptacle 10 relative to base 6 further urges catheter 2 out of outlet 8. In addition, lugs 74 prevent undesirable movement of hub 58 within receptacle 10 during dispensing of catheter 2.

Along these same lines, as seen in FIG. 1, catheter outlet 8 may include integrally molded cylindrical passage 76 in coplanar relationship to wall 49 of base 6. Cylindrical passage 76 is defined at its first end 78 in parallel curvature to the periphery of base 6 and extends tengentially therefrom, and has a lumen therethrough adapted for guiding catheter 2 out of dispenser 4.

As further seen in FIG. 2, tubular member 48 may include an open slot 80 axially disposed along one side, adapted for removing catheter 2. As a result, when base 6 is separated from receptacle 10, catheter 2 may also be totally removed from base 6, so that, following venipuncture and introduction of catheter 2 into the patient, device 4 may be discarded.

Figure 6:
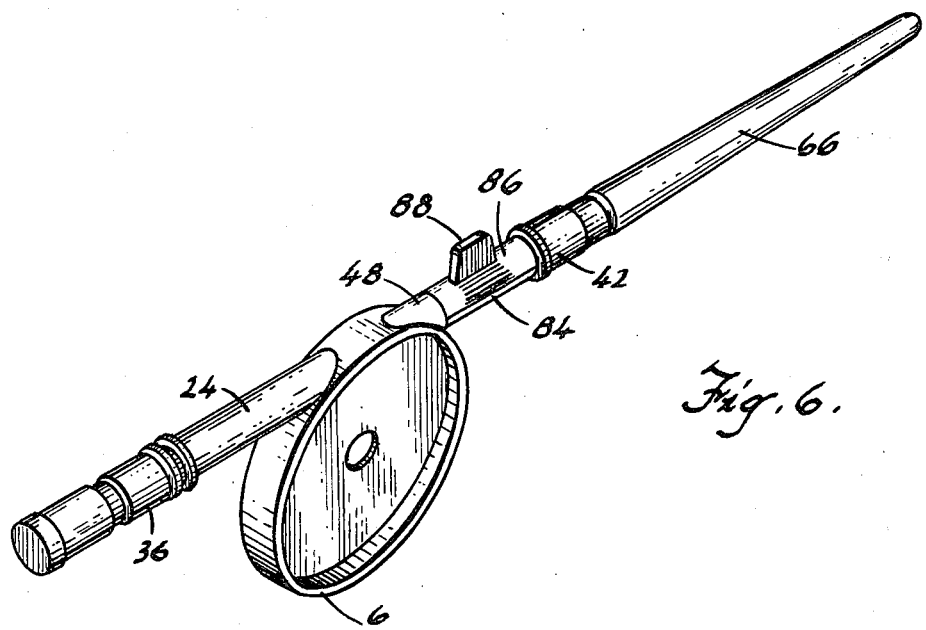
FIG. 6 of the drawings is a perspective view of an additional alternative embodiment of the catheter insertion device of FIG. 1.

In order to accomplish such removal, upper portion 82 and lower portion 84 of tubular member 48 may be pivotable in relation to each other, either by means of a resilient, flexible material or hinged attachment, so that slot 78 may be resiliently openable or resealable as required. Alternatively, tubular member 54 may include a cover 86 attached to and substantially covering slot 78. As an additional alternative best seen in FIG. 6, cover 84 may be snap fit onto lower portion 84 of tubular member 48, so as to serve as the upper portion 82. Cover 84 includes handle 83 to facilitate grasping.

The materials of construction may be any of those conventionally used in catheter assemblies. The entire assembly, with the possible exception of stylet 68 and needle 20 may be formed of molded plastic. By way of specific example, polyethylene, polypropylene or equivalent resins may be used. In choosing a suitable plastic, the catheter and catheter dispenser 4 should preferably be of translucent or transparent plastic, allowing observation of fluid flow and of the length of catheter 2 remaining in receptacle 10. Catheter 2 may be constructed of polyvinyl chloride or of silicone elastomers. Numbers may be printed on the catheter designating increments of length, e.g., inches or centimeters to enable a user to readily determine, by looking at the container and the remaining coils, how much catheter has been advanced into the patient. Likewise, the receptacle may be indexed to indicate the number of revolutions and thereby indicate the length of catheter advanced or remaining. For example, with a catheter having a circumference of five inches, the catheter will be advanced five inches with each rotation of receptacle 10. Needle 20 and stylet 68 may be formed of any suitable materials such as stainless steel, nylon, high density polyethylene or the like.

Operation of the System

In use, sheath 66 is removed, and the combination of needle 20 and cannula 28 are used to perform venipuncture. Needle 20 is then grasped at hub 36 and removed from device 4. Clockwise rotation of receptacle 10 causes catheter 2 to be advanced through cylindrical passage 76, catheter outlet 8 and through cannula 28 into the vein of the patient. Receptacle 10 is then snapped apart from base 6, and coupling socket 44 removed from distal end 46 of catheter outlet 8. Catheter 2 may then be removed entirely from base 6 through slot 80. The final configuration of hub 58, socket 42, cannula 28 and catheter 2 may be seen in FIG. 4, disposed in the arm of a patient.

The foregoing description and drawings merely explain and illustrate the invention, and the invention is not limited thereto, except insofar as the appended claims are limited by those skilled in the art who have the disclosure before them and are able to make modifications and variations therein without departing from the scope of the invention.

I claim:

1. An improved catheter insertion device comprising:
   a catheter dispenser having a base with a catheter outlet extending therefrom and a catheter receptacle including an outwardly facing wall for receiving a catheter therewithin, the dispenser including means engaging the base and receptacle in rotating relation, said catheter being in mechanical engagement with said catheter receptacle whereby rotation of said catheter receptacle relative to said base causes said catheter to be threadably moved through said outlet;
   a tubular housing having an axial bore therethrough tangentially extending from said catheter dispenser in coaxial alignment with said catheter outlet;
   elongate piercing means having a sharpened tip, coaxially disposed through said tubular housing and extending through and beyond said catheter outlet for the performance of venipuncture;
   a hub member affixed to the proximal end of said elongate piercing means constructed and arranged for mating engagement with the distal end of said tubular housing, facilitating the slidable removal of said elongate piercing means from said catheter dispenser; and a cannula member generally contiguously and telescopically surrounding the distal portion of said elongate piercing means and extending beyond said catheter outlet proximate to said sharpened tip, the proximal end of said cannula being in fluid-tight connection to said catheter outlet;

said cannula being operatively associated with said elongate piercing means in performing said venipuncture;

whereupon following said venipuncture, said elongate piercing means may be slidably removed from said cannula and said catheter outlet and said catheter thereupon telescopically inserted into and through said catheter outlet and cannula and into the vein of the patient.

2. The device of claim 1 further comprising a top surface on said base having a central aperture thereon; and a spindle member attached to and extending upwardly from said receptacle and through said central aperture so as to releasably engage said receptacle and base in rotating relation.

3. The device of claim 1 and further comprising:
a female hub member extending from and connected to said tubular housing constructed and arranged for telescopic reception of and press fit attachment to said hub member thereby facilitating selective joinder thereof.

4. The device as disclosed in claim 1 or 2 and further comprising:
a cannula coupling socket having an axial bore therethrough fixedly attached to said cannula member at the proximal end thereof, constructed and arranged for telescopic reception of and press-fit connection to the distal end of said catheter outlet whereby said cannula may be selectively removed from said device as required.

5. The device as disclosed in claim 2 and further comprising:
a catheter hub having an axial bore therethrough fixedly attached to said catheter at its proximal end thereof and adapted for fluid-tight connection to a plurality of intravenous medical equipment sets, as required.

6. The device as disclosed in claim 2 or 5 wherein said base and said catheter receptacle are selectively separable whereby said dispenser may be removed from said catheter subsequent to dispensing of said catheter into the vein of the patient.

7. The catheter dispenser of claim 1 wherein said catheter outlet comprises a tubular member extending tangentially from said base, said catheter outlet being in coaxial alignment with said tubular housing and oppositely disposed therefrom for the telescopic reception of said elongate piercing means therethrough.

8. The device as disclosed in claim 1 and further comprising:
a tubular needle sheath member coaxially disposed about said cannula having the distal portion of said elongate piercing means contained therein, said needle sheath member being telescopically insertable onto the distal end of said catheter outlet so as to enclose and protect said cannula and elongate piercing means therein until the period of use.

9. The device as disclosed in claim 1 wherein said catheter further includes a stiffener extending through said catheter urging said catheter against the inwardly facing wall of the catheter dispenser so as to facilitate dispensing of said catheter when said receptacle is rotated relative to said base.

10. The device of claim 1 wherein said catheter is formed from silicone elastomer.

11. The device as disclosed in claim 1 and further comprising:
a plurality of lug members normally disposed from said receptacle within said dispenser constructed and arranged for fixed positioning of said catheter hub and thereby the transmission of rotational force against said catheter within said dispenser, thereby urging said catheter through said outlet and out of said dispenser upon rotation of said receptacle relative to said base.

12. The device as disclosed in claim 1 wherein said catheter outlet comprises:
an integrally molded cylindrical passage in said catheter base and in coplanar relationship thereto, defined at its first end in parallel curvature to the periphery of said base and tangentially extending therefrom, said cylindrical passage having a lumen therethrough adapted for the guidance of said catheter member out of said dispenser.

13. The device as disclosed in claim 7 wherein said tubular member includes an open longitudinal slot coaxially disposed along one side thereof and adapted for selective removal of said catheter thereby facilitating separation of said catheter from said dispenser following venipuncture.

14. The device as disclosed in claim 13 wherein the upper and lower portions of said tubular member are hingedly connected to each other so as to enable said slot to be resiliently openable and resealable as required.

15. The device as disclosed in claim 13 wherein said tubular member further includes a cover member selectively attached to and substantially covering said slot.

* * * * *